United States Patent [19]

Jackson et al.

[11] Patent Number: 5,696,309
[45] Date of Patent: Dec. 9, 1997

[54] PURIFICATION OF HALOGENATED CARBON COMPOUNDS

[75] Inventors: Andrew Jackson; C. Bradford Boyce, both of Baton Rouge, La.

[73] Assignee: LaRoche Industries, Inc., Baton Rouge, La.

[21] Appl. No.: 423,321

[22] Filed: Apr. 17, 1995

[51] Int. Cl.$^6$ ................................................ C07C 17/38
[52] U.S. Cl. .................... 570/177; 570/178; 570/179; 570/180; 570/247
[58] Field of Search ........................ 570/179, 177, 570/178, 180, 247

[56] References Cited

U.S. PATENT DOCUMENTS

| | | | |
|---|---|---|---|
| 2,498,552 | 2/1950 | Kilgren et al. . | |
| 2,601,322 | 6/1952 | Reese | 570/247 |
| 3,696,156 | 10/1972 | Weeks . | |
| 4,034,049 | 7/1977 | Lovelace . | |
| 4,329,323 | 5/1982 | Shiozaki et al. . | |
| 4,754,088 | 6/1988 | Schmidhammer . | |
| 4,922,042 | 5/1990 | Hoos et al. . | |
| 5,105,035 | 4/1992 | Wang et al. . | |
| 5,221,697 | 6/1993 | Crooker et al. | 570/179 |
| 5,300,714 | 4/1994 | Pothapragada et al. . | |
| 5,449,845 | 9/1995 | Fernandez et al. | 570/177 |

FOREIGN PATENT DOCUMENTS

| | | | |
|---|---|---|---|
| 9191712 | 7/1992 | Australia | 570/177 |
| 370688 | 7/1994 | European Pat. Off. . | |
| 54-19902 | 2/1979 | Japan . | |
| 86387 | 7/1970 | Netherlands . | |
| 685657 | 9/1979 | U.S.S.R. . | |
| 627773 | 8/1949 | United Kingdom . | |
| 1186742 | 4/1970 | United Kingdom . | |

OTHER PUBLICATIONS

Ayscough, P.B. et al, "Photochlorination Studies", 1966, pp. 1838–1845.

Poutsma, M.L. et al, "Chlorination Studies of Unsaturated Materials in Nonplanar Media. I. Solvent Effects on Radical Addition of Chlorine to Chloroethylenes", Union Carbide Research Institute, Union Carbide Corp., Tarrytown, NY, Sep. 20, 1964, pp. 3807–3814.

*Primary Examiner*—Alan Siegel
*Attorney, Agent, or Firm*—Andrew Alexander

[57] ABSTRACT

Disclosed is a method of chlorinating vinylidene chloride contained in a solution 1,1-dichloro-1-fluoroethane to provide a chlorinated compound having a boiling point different from the 1,1-dichloro-1-fluoroethane to permit separation therefrom. The method comprises providing a solution containing 1,1-dichloro-1-fluoroethane and vinylidene chloride; introducing chlorine to the solution; and contacting the chlorine containing solution with a metal oxide to effect chlorination of the vinylidene chloride to produce one of 1,1,1,2-tetrachloroethane, trichloroethylene and pentachloroethane.

35 Claims, No Drawings

PURIFICATION OF HALOGENATED CARBON COMPOUNDS

BACKGROUND OF THE INVENTION

This invention relates to a method of purifying 1,1-dichloro-1-fluoroethane by removal of unsaturated carbon compounds such as vinylidene chloride having the same or similar boiling points.

In the prior art, 1,1-dichloro-1-fluoroethane, sometimes referred to by the designation HCFC-141b, has been prepared by the reaction of vinylidene chloride with hydrogen fluoride. Often after the reaction, traces of unreacted vinylidene chloride, as well as various other unsaturated organic impurities, remain in the 1,1-dichloro-1-fluoroethane and cannot be easily separated therefrom by distillation or other means because they have similar boiling points. Vinylidene chloride has a boiling point of 31.7° C. and 1,1-dichloro-1-fluoroethane has a boiling point of 32.1° C., and thus they are difficult to separate by distillation. It is particularly desirable to remove vinylidene chloride because it is toxic and is considered to be a carcinogen.

Various methods have been proposed for removing unsaturated organic compounds, such as vinylidene chloride from saturated hydrohalofluorocarbons. For example, U.S. Pat. No. 5,105,035 discloses a process for removing vinylidene chloride and other unsaturated impurities from HCFC-141b by reaction with hydrogen over a catalyst such as palladium on alumina. However, this process can result in a loss of HCFC-141b by dechlorination which results from excessive hydrogenation and hydrodechlorination.

U.S. Pat. No. 5,300,714 discloses a method of removing olefinic impurity, such as perfluoroisobutylene, from fluoroperhalocarbon liquid, such as perfluorinated liquid. The method comprises the step of contacting the fluoroperhalocarbon liquid with a body of particles comprising particles selected from the group consisting of alumina, alkali metal oxide, alkali metal hydroxide, alkaline earth oxide, alkaline earth hydroxide, silicon oxide, tin oxide, zinc oxide, alkaline earth basic carbonate, and alkaline earth basic phosphate, transition metal oxide particles and mixtures thereof.

European Patent 39311839 (1989),discloses purification of saturated fluorohalocarbons containing unsaturated impurities by the use of metal oxides to oxidize unsaturated impurities to carbon dioxide.

U.S. Pat. No. 4,754,088 discloses a process for oxychlorination of ethylene wherein 1,2-dichloroethane is prepared by chlorination of ethylene-containing reaction vent gases from the oxychlorination of ethylene in the presence of a catalyst carrier impregnated with metal compounds wherein the waste from the oxychlorination stage are chlorinated, the improvement comprising preheating the ethylene-containing waste gases to at least 50° C. and then chlorinating the ethylene at 100° to 300° C. at a pressure of 1 to 7 bar with a space velocity of 100 to 5000 h$^{-1}$ related to standard conditions in the presence of at least one metal compound selected from the group consisting of chlorides and oxides of manganese, nickel and cobalt supported on a catalyst cattier with reduced formation of oxychlorinated by-products.

U.S. Pat. No. 4,329,323 discloses a process for removing ethylene and vinyl chloride from a gas stream containing them by passing a mixed gas containing ethylene, vinyl chloride and a necessary amount of chlorine through a fixed-bed reactor charged with, as a catalyst, an activated alumina supporting at least 4% by weight of ferric chloride in terms of iron, the catalyst having an outer surface area per unit packed catalyst volume of not less than 7.8 cm$^2$/ml. Ethylene and vinyl chloride are converted into and removed as 1,2-dichloroethane and 1,1,2-trichloroethane. The concentrations of ethylene and vinyl chloride can be decreased to not more than 10 ppm and not more than 20 ppm, respectively.

U.S. Pat. No. 2,498,552 discloses a process for the chlorination of normally gaseous paraffinic hydrocarbons which comprises introducing the hydrocarbon to be chlorinated and chlorine into a chlorination zone, introducing cupric oxychloride into the chlorination zone, maintaining a temperature within the range of from about 325° C. to about 500° C. in the chlorination zone, regulating the rate of introduction of the cupric oxychloride so that at least one mole of oxychloride is introduced per mole of chlorine introduced thereto, and recovering the chlorinated hydrocarbons from the gaseous effluent from the chlorination zone.

U.S. Pat. No. 4,034,049 discloses meso-1,2,3,4-tetrachlorobutane produced in an improved liquid phase chlorination process wherein the trans-1,4-dichlorobutene-2 is contacted with chlorine in the presence of a catalytic amount of molybdenum.

U.S. Pat. No. 4,922,042 discloses a process for the production of 1,2-dichloroethane by the reaction between ethylene and chlorine in the vapor phase in the presence of a catalyst comprising alma, wherein the reaction is carded out using a fluidized bed comprising fluidizable, substantially spherical particles of alumina of surface area not exceeding 10 m$^2$g$^{-1}$ and especially in the range 0.2 to 6 m$^2$g$^{-1}$.

British Patent 627,773 (1949) discloses the separation of 1,1-dichloro-1-fluoroethane from its admixture with vinylidene chloride by chlorination of the vinylidene chloride and recovery of the 1,1-dichloro-1-fluoroethane by distillation.

Poutsma et al in an article entitled "Chlorination Studies of Unsaturated Materials in Nonpolar Media. I. Solvent Effects on Radical Addition of Chlorine to Chloroethylenes" disclose that the relative rates of addition of chlorine atom to 1,1-dichloroethylene, cis-and trans-1,2-dichloroethylene, trichloroethylene, and tetrachloroethylene in noncomplexing solvents have been measured both directly by competitive photochlorination of pairs of olefins and indirectly by comparison of addition to each olefin in competition with hydrogen abstraction from cyclohexane. The selectivity of chlorine atom with respect to such radical addition has been found to be substantially increased by the presence of the complexing solvents benzene and carbon disulfide. Solvent dependence has also been demonstrated for the competition between addition to the olefins and hydrogen abstraction from cyclohexane; attempts to extend such solvent effects to competitive addition and abstraction behavior of the trichloromethyl radical were unsuccessful.

In spite of these prior processes, there is still a great need for an economic, efficient process that enables separation of vinylidene chloride, for example, from 1,1-dichloro-1-fluoroethane. The present invention provides such a process.

SUMMARY OF THE INVENTION

It is an object of this invention to provide a process for purifying 1,1-dichloro-1-fluoro ethane.

It is another object of this invention to provide an improved process for chlorination of vinylidene chloride contained in 1,1-dichloro-1-fluoroethane.

It is yet another object of this invention to provide an improved process for converting vinylidene chloride to a saturated compound that has a boiling point sufficiently different from 1,1-dichloro-1-fluoroethane to permit separation thereof from 1,1-dichloro-1-fluoroethane by distillation, for example.

These and other objects will become apparent from the specification and claims appended hereto.

In accordance with these objects, there is provided a method of chlorinating vinylidene chloride contained in a solution 1,1-dichloro-1-fluoroethane to provide a chlorinated compound having a boiling point different from the 1,1-dichloro-1-fluoroethane to permit separation therefrom. The method comprises providing a solution containing 1,1-dichloro-1-fluoroethane and vinylidene chloride; introducing chlorine to the solution to provide chlorine in the solution; and contacting the chlorine and the solution with a metal oxide to effect chlorination of the vinylidene chloride to produce one of 1,1,1,2-tetrachloroethane, trichloroethylene and pentachloroethane. The 1,1 dichloro-1-fluoroethane is useful as a foam blowing agent and as a solvent in various applications.

DETAILED DESCRIPTION OF PREFERRED EMBODIMENTS

When 1,1-dichloro-1-fluoroethane is produced by reaction of vinylidene chloride or trichloroethane with hydrogen fluoride, the 1,1-dichloro-1-fluoroethane can contain up to 9000 ppm or higher residual vinylidene chloride. Other by-products may be present in lesser amounts; however, it is particularly important to remove vinylidene chloride because of its toxicity. 1,1-dichloro-1-fluoroethane has been found useful as a replacement for trichlorofluoromethane as a foam blowing agent and such use requires that it be substantially free of toxic vinylidene chloride. That is, the level of vinylidene chloride should be reduced to not more than 200 ppm, preferably less than 100 ppm.

In the process of the invention, vinylidene chloride and other unsaturated compounds are chlorinated. When vinylidene chloride is chlorinated, it reacts to produce 1,1,1,2-tetrachloroethane and trichloroethylene. Further chlorination can convert the trichloroethylene to pentachloroethane. 1,1,1,2-tetrachloroethane has a boiling point of 130.5° C.; trichloroethylene has a boiling point of 88° C. and pentachloroethane boils at 162° C. Because these compounds have boiling points substantially different from 1,1 dichloro-1-fluoroethane, (boiling point 32.1° C.), they can be easily separated from 1,1 dichloro-1-fluoroethane by distillation, for example. It should be noted that unsaturated organic compounds other than vinylidene chloride may be chlorinated in a similar way to provide the saturated equivalents.

In the process of the present invention, 1,1-dichloro-1-fluoroethane in the liquid phase containing vinylidene chloride can be contacted with chlorine in the presence of a metal oxide catalyst. For purposes of contacting, 1,1-dichloro-1-fluoroethane may be present in the liquid form.

In the present invention, a body of 1,1-dichloro-1-fluoroethane containing vinylidene chloride and other unsaturated organic compounds is first contacted with a source of chlorine to provide chlorine for chlorination in accordance with the invention. The chlorine is added in an amount sufficient to chlorinate vinylidene chloride and other unsaturated compounds in the 1,1-dichloro-1-fluoroethane.

In the present invention, chlorine is preferably added to the 1,1-dichloro-1-fluoroethane solution to provide a molar ratio in the range of about 1:1 to 5:1, preferably 1:1 to 3:1, chlorine to vinylidene chloride in the solution. Preferably, the chlorine is provided in excess of the vinylidene chloride to permit other unsaturated impurities to be reacted. Further, preferably, the chlorine is added at about ambient temperature and further, preferably the chlorine is added in gaseous form.

After chlorine has been added to the 1,1-dichloro-1-fluoroethane solution, the combination is passed through a bed of metal oxide particles. The metal oxide particles are effective in catalyzing the chlorination of the vinylidene chloride and other unsaturated compounds to provide saturated compounds with boiling points substantially different from that of 1,1-dichloro-1-fluoroethane.

For purposes of chlorination, the catalytic reaction can be carded out in a temperature range of about 0° to 100° C. and preferably in a temperature range of 10° to 60° C. However, while these temperatures are provided as guides, any temperature may be used which effectively permits chlorination to the equivalent saturated compound. Thus, for purposes of chlorination, a stream of chlorine treated 1,1-dichloro-1-fluoroethane is introduced to the metal oxide catalyst in these temperature ranges.

While the stream of chlorine treated 1,1-dichloro-1-fluoroethane can be substantially free of water, it is preferred that water be added to the stream to provide a water concentration of less than 3000 ppm and preferably in the range of about 20 ppm to 3000 ppm and typically 20 to 2000 ppm. However, the amount of water present should be controlled to avoid blocking active sites in the metal oxide catalyst that promote the chlorination process.

In a preferred embodiment of the invention, the metal oxide catalyst is treated or saturated with chlorine prior to contacting the catalyst with the 1,1-dichloro-1-fluoroethane containing vinylidene chloride. By pretreating the catalyst with chlorine, the chlorination process is more efficient by providing chlorine more readily available for reaction. The metal oxide catalyst may be contacted with a fluid containing chlorine for treatment purposes. For example, the treatment may be carried out by contacting the metal oxide catalyst with 1,1-dichloro-1-fluoroethane saturated with chlorine.

The metal oxide catalyst useful in the invention may be any metal oxide that can effect chlorination of the unsaturated organic compound, e.g., vinylidene chloride, to produce the saturated equivalent compound. Metal oxides that have been found useful in the chlorination process of the present invention include $TiO_2$, CuO, $MnO_2$, $KMnO_4$, CoO, AgO and FeO. Preferred metal oxides comprise a mixture of two or more of these metal oxides. For example, combinations of flash calcined active alumina (FCA) and $MnO_2$ are suitable in the range of 1 to 6 parts $MnO_2$ to 1 to 6 parts FCA, with a preferred metal oxide having 5 parts FCA and 2 parts $MnO_2$ (referred to as 5/2 FCA). Another suitable mixed oxide comprises 1 to 5 parts CuO to 1 to 10 $MnO_2$ with a preferred metal oxide having 2 parts CuO and 9 parts $MnO_2$. This mixed oxide is available from Callery Chemical Company, P.O. Box 429, Pittsburgh, Pa. 15230 under the tradename Hopcalite®. Yet another suitable mixed oxide comprises 1 to 2 parts CuO, 3 to 9 parts $MnO_2$, 1 to 2 parts $Al_2O_3$ with a preferred metal oxide having 1.5 parts CuO, 6 parts $MnO_2$, 1 part $Al_2O_3$. This mixed oxide is available from Cams Chemical Company, LaSalle, Ill. 61301 under the tradename Camlite®. A further type mixed oxide suitable in the present invention comprises 0.5 to 3 parts $KMnO_4$ and 5 to 12 parts $Al_2O_3$, with a preferred mixed oxide comprising I part $KMnO_4$ and 10 parts $Al_2O_3$. The $KMnO_4/Al_2O_3$ type mixed oxide is available from Cams Chemical Company, LaSalle, Ill. 61301 under the tradename Camsorb®. The TiO₂ suitable in the invention is available from LaRoche Industries, Inc., Baton Rouge, La. 70821, under the designation S-701®.

The metal oxide catalysts may be provided on or mixed with alumina supports or may be used without alumina supports. The alumina supports can comprise alumina trihydrate, pseudoboehmite, alpha alma monohydrate, and thermal activated aluminas having gamma, eta, chi-rho-eta, delta or kappa structures. The aluminas suitable for supports have a surface area of greater than 80 m²/gm and preferably have a surface area in the range of 100 to 350 m²/gm. Further, preferably, the alma supports have a pore volume in the range of 0.3 to 1 cm³/gm. Alma supports useful in the present invention are available from LaRoche Industries, Inc., Baton Rouge, La. 70821, under the designation Versal®.

While the inventors do not wish to be bound by any theory of invention and while they do not fully understand the process of chlorination of the invention, it is believed that the schemes for chlorinating vinylidene chloride in 1,1-dichloro-1-fluoroethane are as follows:

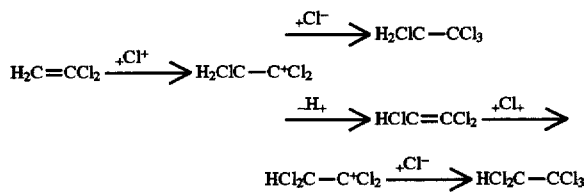

The metal oxides coated on alumina supports used for catalytic purposes are preferably provided in a bed through which the combination of chlorine and 1,1-dichloro-1-fluoroethane can be suitably passed through.

In the present invention, the flow rate of 1,1-dichloro-1-fluoroethane to the bed of metal oxide catalysts should be controlled to provide a residence time in the range of 5 to 60 minutes with typical residence time of 15 to 25 minutes having been found to be suitable.

In addition, while chlorine is preferably mixed with 1,1-dichloro-1-fluoroethane prior to being introduced to the bed, it will be understood that the chlorine may be introduced to the 1,1-dichloro-1-fluoroethane just prior to being introduced to the bed of metal oxide catalyst. Or, the chlorine can be added to the bed independent of the 1,1-dichloro-1-fluoroethane. Further, the bed comprising metal oxide catalyst, 1,1-dichloro-1-fluoroethane and chlorine may be kept under pressure effect chlorination.

The following examples are still further illustrative of the invention.

EXAMPLE 1

To test the effectiveness of different metal oxides to effect reaction of chlorine with vinylidene chloride in a 1,1-dichloro-1-fluoroethane solution, several glass columns were prepared. The four glass columns were 0.5 inch ID and 3 inches long and each was filled with different metal oxide catalyst: Camsorb®, 5/2 FCA, Camlite®, and Hopcalite®. Each catalyst was conditioned with chlorine by passing 1,1-dichloro-1-fluoroethane containing 1 wt. % chlorine through the catalyst. The solution was passed through the catalyst for about 1 to 2 hours. Then; a solution of 1,1-dichloro-1-fluoroethane containing about 2:1 molar ratio of chlorine to vinylidene chloride was passed through the columns for a period to provide a residence time of 20 minutes. The solution was then treated with sodium sulfite to remove excess chlorine. Thereafter, the solutions were analyzed by gas-liquid chromatography with a detection limit of 1 ppm and results reported as area%. The effectiveness of the different catalysts in the chlorination of vinylidene chloride is shown in Table 1 where the amount of vinylidene chloride is reported "before" chlorination and "after" chlorination.

TABLE 1

| Sample | Before* | After* |
|---|---|---|
| Camsorb ®3 | 0.3743 | NF¹ |
| 5/2 FCA² | 0.3588 | NF¹ |
| Carulite ® | 0.3312 | 0.0025 |
| Hopcalite ® | 0.3312 | 0.0035 |

*values for vinylidene chloride present and reported as area %
¹not found (detection limit 1 ppm)
²five parts manganese dioxide to two parts flash calcined active alumina
³heated 1 hour at 200°

It will be seen from Table 1 that Camsorb® and 5/2 FCA were more effective in catalyzing chlorination of vinylidene chloride. It should be noted that Camsorb® was heated for 1 hour at 200° C. to liberate manganese (IV) dioxide from a potassium permanganese complex.

EXAMPLE 2

This example was the same as Example 1 except the chlorine:vinylidene mole ratio was 1:1. The results are shown in Table 2 for vinylidene chloride present in 1,1-dichloro-1-fluoroethane "before" chlorination and "after" chlorination.

TABLE 2

| Sample | Before* | After* |
|---|---|---|
| Camsorb ®1 | 76.84 | 5.66 |
| 5/2 FCA² | 18.15 | 0.65 |
| Carulite ® | 18.15 | 0.52 |

*values are reported as area % normalized to an internal standard at 0.05%
¹heated 1 hour at 200° C.
²five parts manganese dioxide to two parts flash calcined active alumina

EXAMPLE 3

This example was the same as Example 1 except the test was run to examine catalyst activity over an extended period. Thus, four liter samples were prepared by dissolving 0.605 mol of chlorine gas and 0.303 mol vinylidene chloride in 1,1-dichloro-1-fluoroethane. These samples were passed through beds of Camsorb® and Versal® over a 30-day period. In both cases, vinylidene chloride was consistently reduced below the 20 ppm level throughout the 30-day period.

EXAMPLE 4

This example was performed as in Example 1 to test the capability of metal oxide catalyst to chlorinate vinylidene chloride to trichloroethylene and to pentachloroethane. The metal oxides were compared to activated alma, available from LaRoche Industries, Inc., Baton Rouge, La. 70821, under the designation A-201. Concentration of the chlorine to vinylidene chloride in the 1,1-dichloro-1-fluoroethane solution was in a mole ratio of 2:1. The results are shown in Table 3.

TABLE 3

| Sample | Vinylidene chloride | | Trichloroethylene | | Pentachlorethane | |
|---|---|---|---|---|---|---|
| | Before | After | Before | After | Before | After |
| A-201 ®[2] | 0.54 | nf[3] | 0.08 | 0.22 | nf[3] | nf[3] |
| Carusorb ®[1] | 81.39 | nf[3] | 0.13 | 39.79 | 0.35 | 0.97 |
| Carulite ® | 4.73 | 0.04 | 0.02 | 3.11 | 0.09 | 1.14 |

*values reported as area % normalized to an internal standard at 0.05%
[1]heated 1 hour at 200° C.
[2]values reported as area %
[3]not found (detection limit 1 ppm)

It will be seen that the alumina was effective in the chlorination of vinylidene chloride to trichloroethylene but not effective in converting trichloroethylene to pentachloroethane.

While the invention has been described in terms of preferred embodiments, the claims appended hereto are intended to encompass other embodiments which fall within the spirit of the invention.

What is claimed is:

1. A method of chlorinating vinylidene chloride contained in a solution 1,1-dichloro-1-fluoroethane, excluding photochlorination to provide a chlorinated compound having a boiling point different from the 1,1-dichloro-1-fluoroethane to permit separation therefrom, the method comprising:

(a) providing a solution containing 1,1-dichloro-1-fluoroethane and vinylidene chloride;

(b) introducing chlorine to said solution to provide chlorine therein; and (c) contacting said chlorine and said solution with a metal oxide to effect chlorination of said vinylidene chloride to produce one of 1,1,1,2-tetrachloroethane, trichloroethylene and pentachloroethane.

2. The method in accordance with claim 1 including adding chlorine to said solution in a mole ratio of 1:1 to 5:1 chlorine to vinylidene chloride.

3. The method in accordance with claim 1 including adding chlorine to said solution in a mole ratio of 1:1 to 3:1 chlorine to vinylidene chloride.

4. The method in accordance with claim 1 including contacting effected in a temperature range of 0° to 100° C.

5. The method in accordance with claim 1 including contacting effected in a temperature range of 10° to 60° C.

6. The method in accordance with claim 1 including maintaining water in said solution at less than 3000 ppm.

7. The method in accordance with claim 1 including maintaining water in said solution in the range of 20 to 3000 ppm.

8. The method in accordance with claim 1 including conditioning said metal oxides prior to effecting chlorination by treating said metal oxides with chlorine.

9. The method in accordance with claim 8 including conditioning said metal oxides by contacting with a 1,1-dichloro-1-fluoroethane solution containing chlorine.

10. The method in accordance with claim 1 wherein said vinylidene chloride in said solution is reduced to less than 200 ppm.

11. The method in accordance with claim 1 wherein said vinylidene chloride in said solution is reduced to less than 100 ppm.

12. The method in accordance with claim 1 wherein said contacting is for a period of less than 2 hours.

13. The method in accordance with claim 1 wherein said metal oxide is at least one of the group consisting of $TiO_2$, CuO, $MnO_2$, CoO, AgO and FeO and combinations thereof.

14. The method in accordance with claim 1 wherein said metal oxide is a combination of metal oxides, the combination selected from the group consisting of $Al_2O_3$—$MnO_2$; CuO—$MnO_2$; CuO—$MnO_2$—$Al_2O_3$; $TiO_2$.

15. The method in accordance with claim 1 wherein said metal oxide is provided as an alumina support.

16. The method in accordance with claim 15 wherein the alumina support has a surface area of at least 80 m²/g.

17. The method in accordance with claim 15 wherein the alumina support has a surface area in the range of 100 to 350 m²/gm.

18. A method separating vinylidene chloride from a 1,1-dichloro-1-fluoroethane, excluding photochlorination solution comprising the steps of:

(a) providing a solution of 1,1-dichloro-1-fluoroethane containing vinylidene chloride;

(b) adding chlorine to said solution to provide a chlorine containing solution;

(c) passing said chlorine containing solution through a bed comprised of metal oxides to effect chlorination of said vinylidene chloride; and (d) separating said chlorinated vinylidene chloride from said 1,1-dichloro-1-fluoroethane solution.

19. The method in accordance with claim 18 including separating by distillation.

20. The method in accordance with claim 18 including adding chlorine to said solution in a mole ratio of 1:1 to 5:1 chlorine to vinylidene chloride.

21. The method in accordance with claim 18 including adding chlorine to said solution in a mole ratio of 1:1 to 3:1 chlorine to vinylidene chloride.

22. The method in accordance with claim 18 including contacting effected in a temperature range of 0° to 100° C.

23. The method in accordance with claim 18 including contacting effected in a temperature range of 10° to 60° C.

24. The method in accordance with claim 18 including maintaining water in said solution at less than 200 ppm.

25. The method in accordance with claim 18 including maintaining water in said solution in the range of 20 to 100 ppm.

26. The method in accordance with claim 18 including conditioning said metal oxides prior to effecting chlorination by treating said metal oxides with chlorine.

27. The method in accordance with claim 8 including conditioning said metal oxides by contacting with a 1,1-dichloro-1-fluoroethane solution containing chlorine.

28. The method in accordance with claim 18 wherein said vinylidene chloride in said solution is reduced to less than 200 ppm.

29. The method in accordance with claim 18 wherein said vinylidene chloride in said solution is reduced to less than 100 ppm.

30. The method in accordance with claim 18 wherein said contacting is for a period of less than 2 hours.

31. The method in accordance with claim 18 wherein said metal oxide is at least one of the group consisting of $TiO_2$, CuO, $MnO_2$, CoO, AgO and FeO and combinations thereof.

32. The method in accordance with claim 18 wherein said metal oxide is a combination of metal oxides, the combination selected from the group consisting of $Al_2O_3$-$MnO_2$; CuO—$MnO_2$; CuO—$MnO_2$—$Al_2O_3$; $TiO_2$.

33. The method in accordance with claim 18 wherein said metal oxide is provided as an alumina support.

34. The method in accordance with claim 18 wherein the alumina support has a surface area of at least 80m²/gm.

35. The method in accordance with claim 18 wherein the alumina support has a surface area in the range of 100 to 350 m²/gm.

* * * * *